United States Patent

Dossett

[11] Patent Number: 5,750,456
[45] Date of Patent: May 12, 1998

[54] CATALYST COMPOSITION FOR PREPARING POLYKETONES

[75] Inventor: Stephen John Dossett, Aldershot, England

[73] Assignee: BP Chemicals Limited, London, England

[21] Appl. No.: 622,586

[22] Filed: Mar. 26, 1996

[30] Foreign Application Priority Data

Mar. 29, 1995 [GB] United Kingdom ............. 9506378

[51] Int. Cl.$^6$ .................. B01J 31/00; C07F 15/00; C07F 17/02; C07F 15/02

[52] U.S. Cl. .................. 502/155; 502/159; 556/7; 556/19; 556/20; 556/27; 556/28; 556/136; 556/138; 528/392

[58] Field of Search ................ 556/7, 14, 27, 556/20, 28, 136, 138, 146; 502/154, 155, 162

[56] References Cited

U.S. PATENT DOCUMENTS

| | | | |
|---|---|---|---|
| 3,415,762 | 12/1968 | Block et al. | 556/20 |
| 3,415,781 | 12/1968 | Block et al. | 556/20 |
| 3,457,195 | 7/1969 | Block et al. | 556/20 |
| 3,694,412 | 9/1972 | Nozaki | 260/63 CQ |
| 4,824,934 | 4/1989 | Van Broekhoven et al. | 502/154 |
| 4,831,113 | 5/1989 | Van Broekhoven et al. | 502/154 |
| 4,859,644 | 8/1989 | Van Broekhoven et al. | 502/154 |

FOREIGN PATENT DOCUMENTS 0 121 965  10/1984  European Pat. Off. .

*Primary Examiner*—Glenn Caldarola
*Assistant Examiner*—J. Pasterczyk
*Attorney, Agent, or Firm*—Fay, Sharpe, Beall, Fagan, Minnich & McKee

[57] ABSTRACT

A catalyst composition suitable for use in a process for the preparation of polyketones comprising a group VIII metal complex of a phosphonite of formula (I)

$$R^1R^2E(OPR^3_2)_2^{-1} \quad (I)$$

where $R^1$ and $R^2$ are independently a halide or a hydrocarbyl.

$R^3$ is an optionally substituted hydrocarbyl

E is boron, aluminium or gallium.

Preferred compositions are $[F_2B(OPPh_2)_2PdCl]_2$ and $[F_2B(OPPh_2)_2 Pd(NCPh)_2]^+[BF_4]^-$.

8 Claims, No Drawings

CATALYST COMPOSITION FOR PREPARING POLYKETONES

The present invention relates to a catalyst composition suitable for use in the process for the preparation of interpolymers of olefins and carbon monoxide.

The preparation of linear alternating interpolymers of olefins and carbon monoxide having the general formula:

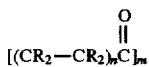

where the R groups are independently hydrogen or hydrocarbyl groups, n is at least 1 and m is a large integer, is known from U.S. Pat. No. 3,694,412. Such linear alternating interpolymers, which hereinafter will be called polyketones, are prepared according to U.S. Pat. No. 3,694,412 by polymerising a mixture of one or more olefins and carbon monoxide in the presence of an aryl phosphine complex of a palladium halide and an inert solvent. The processes described in the U.S. Pat. No. 3,694,412 are however slow even at elevated temperature and pressure.

An improved version of the above process is described in European Patent Application No. 0121965. It was subsequently found that the rate of the polymerisation could be increased considerably by using a palladium catalyst with inter alia a bidentate phosphine ligand having a divalent organic bridging group having at least two carbon atoms in the bridge and an acid with a pKa of less than 2.

We have now found that instead of using a ligand having a divalent organic bridging group, catalyst systems based upon a phosphinite ligand may be used for the production of polyketones.

According to the present invention there is provided a catalyst composition suitable for use in the process for the preparation of polyketones comprising a Group VIII metal complex of a phosphinite of formula (I)

$$R^1R^2E(OPR_2^3)_2^{-1} \qquad (I)$$

where $R^1$ and $R^2$ are independently a halide or a hydrocarbyl.

$R^3$ is an optionally polar substituted hydrocarbyl group
E is boron, aluminium or gallium.

According to a further aspect of the present invention, there is provided a process for the preparation of polyketones which comprises polymerising a mixture of carbon monoxide and one or more olefins in the presence of a catalyst composition as defined above.

The term polyketone is used herein to mean an interpolymer of one or more olefins with carbon monoxide. The idealised structure of such a material would comprise a one, two or three dimensional network of strictly alternating olefin and carbon monoxide units. Although polyketones prepared according to the present invention correspond to this idealised structure, it is envisaged that materials corresponding to this structure in the main but containing small regimes (i.e. up to 10wt %) of the corresponding polyolefin also fall within the definition.

The catalyst comprises a Group VIII metal. The Group VIII metals are iron, cobalt, nickel, ruthenium, rhodium, palladium, osmium, iridium and platinum. The second row Group VIII metals (i.e. ruthenium, rhodium, palladium) are preferred; particularly preferred is palladium.

$R^1$ and $R^2$ are independently a halide or a hydrocarbyl. Where $R^1$ and $R^2$ are independently a halide, the halide is preferably fluoride. Where $R^1$ and $R^2$ are independently a hydrocarbyl, $R^1$ and $R^2$ are preferably phenyl.

$R^3$ is an optionally polar substituted hydrocarbyl. Preferably $R^3$ is phenyl.

The present invention is a catalyst composition comprising a group VIII metal complex of a phosphinite. Suitably the composition is a dimeric complex as defined in Formula (II)

$$[R^1R^2E(OPR_2^3)M^2X]_2 \qquad (II)$$

where $R^1$, $R^2$, E and $R^3$ are as defined above
$M^2$ is a group VIII metal
X is a halide, preferably chloride.

By way of example a catalyst of the specific formula $$[F_2B(OPPh_2)_2PdCl]_2$$

may be used as the catalyst in the polymerisation process.

The composition may also be as defined in Formula (III)

$$[R^1R^2E(OPR_2^3)M^2L_2] \qquad (III)$$

where $R^1$, $R^2$, E, $R^3$ and $M^2$ are as defined above and L is a labile donor ligand; for example benzonitrile, acetonitrile, water and acetone.

It will of course be understood by the skilled addressee that such compounds will be cationic and thus will be present with a suitable anionic species, for example an anion of an acid of pKa<6, preferably pKa<2, e.g. $PF_6^-$, trifluoroacetate, tosylate or $BF_4^-$. Preferably, the anion is $BF_4^-$.

By way of example, catalyst of the specific formula $$[F_2B(OPPh_2)_2Pd(NCPH)_2]^+[BF_4]^-$$

may be used as the catalyst in the polymerisation process.

The composition may also be defined as in Formula (IV)

$$[R^1R^2E(OPR_2^3)M^2LX] \qquad (IV)$$

where $R^1$, $R^2$, E, $R^3$, $M^2$, L and X are as defined above. Preferably X is a halide, e.g. chloride.

In the process for preparing a polyketone using the aforementioned catalyst, there may also be present a cocatalyst. Such a cocatalyst may be either a Bronsted or a Lewis acid. Where the cocatalyst is a Bronsted acid it is preferably an acid having a pKa of less than 2 e.g. $HBF_4$. Where the cocatalyst is a Lewis acid it is preferably a Boron Lewis e.g. $BF_3$ or a boron hydrocarbyl.

Considering the feedstock for the polymerisation reaction, it is believed that any source of carbon monoxide can be used. Thus, the carbon monoxide may contain nitrogen, inert gases and up to 10% hydrogen.

Any olefin can, be used. Preferably ethylene or a mixture of olefins, e.g. ethylene and propylene and the like may be used. A preferred polyketone is a terpolymer of ethylene, propylene and carbon monoxide:

The polymerisation process is suitably carried out in a solvent which is chemically inert under the conditions employed and one in which the catalyst is soluble. Moreover, the solvent like the anion should be either weakly coordinating or non-coordinating. Examples of such solvents include alcohols e.g. methanol, ethanol and propanol, ethers, glycol ethers and chlorinated solvents e.g. chloroform and dichloromethane. Preferred solvents are methanol, ethoxyethanol, chloroform or dichloromethane; especially dichloromethane. Alternatively, an aliphatic tertiary alcohol can be used, preferably tertiary butanol. This can be used as a solvent on its own or in combination with an aprotic solvent, for example ketones. A preferred solvent system is dichloromethane.

The polymerisation process is suitably carried out at a temperature in the range of from 20° to 150° C., preferably 50° to 120° C. and at elevated pressure of from 1 to 100 bar. The over pressure of the gas is suitably carbon monoxide or carbon monoxide and olefin, if the olefin is gaseous under the reaction conditions. It is possible to operate the polymerisation process either batchwise or continuously.

The present invention is further illustrated by way of the following examples.

Example 1

Preparation of $[Pd((PPh_2O)_2BF_2)Cl]_2$ $HBF_4OEt_2$ (64 µl, $3.7 \times 10^{-4}$ mol) was added dropwise to a stirred suspension of $[Pd((PPh_2O)_2H)Cl]_2$ (0.2 g, $1.8 \times 10^{-4}$ mol) in acetone (20 ml) at room temperature. A clear solution resulted which was stirred for 20 minutes. Then the solvent was then removed in vacuo to ca 5 ml. Diethylether was added (25 ml) to precipitate the complex as buff microcrystals $[Pd((PPh_2O)_2BF_2)Cl]_2$ (0.15 g, $1.3 \times 10^{-4}$ mol).

Example 2

Preparation of $[Pd((PPh_2O)_2BF_2)(NCPh)_2][BF_4]$

To a solution of $[Pd((PPh_2O)_2BF_2)Cl]_2$ (0.2 g, $1.7 \times 10^{-4}$ mol) in $CH_2Cl_2$ (20 ml), $AgBF_4$ (0.066 g, $3.4 \times 10^{-4}$ mol), and PhCN (0.17 ml, $1.7 \times 10^{-3}$ mol) was added. The mixture was stirred for one hour during which time a precipitate of AgCl was formed. The solution was filtered and the solvent reduced in volume in vacuo to ca 5 mls.

Addition of diethylether (25 ml) resulted in white microcrystals of $[Pd((PPh_2O)_2BF_2)(NCPh)_2][BF_4]$ (0.107 g, $1.36 \times 10^{-4}$ mol).

Example 3

Polymerisation of Carbon Monoxide and Ethylene and Propene

Tris (pentafluorophenyl) boron, (0.086 gm 0.16 mmol) was dissolved in degassed dichloromethane, and transferred to a 300 cm³ Autoclave Engineers reactor under nitrogen. Propene, (25.6 g 0.61 mol) was introduced into the autoclave. The stirred reactor contents were pressured to 40 barg with a 1:1 mixture of carbon monoxide and ethylene and heated to 70° C. A solution of $[BF_2(OPPh_2)_2PdCl]_2$, (0.020 g 0.017 mmol) in degassed dichloromethane (10 cm³) was introduced into the reactor and the pressure was adjusted to 50 barg by addition of 1:1 $CO/C_2H_4$. During the subsequent reaction, a pressure of 50 barg was maintained by the addition of $CO/C_2H_4$. Three hours after the addition of the palladium, the reaction was stopped by cooling the mixture and venting the gaseous components. The alternating ethylene/propylene/CO polymer was collected by filtration and dried in vacuo.

I claim:

1. A catalyst composition suitable for use in a process for the preparation of polyketones comprising a Group VIII metal complex of a phosphinite of formula (I):

$$R^1R^2E(OPR^3_2)_2^{-1} \qquad (I)$$

where $R^1$ and $R^2$ are independently a halide or a hydrocarbyl;

$R^3$ is a hydrocarbyl group optionally substituted with a polar group; and E is boron, aluminum or gallium.

2. A catalyst composition as claimed in claim 1 wherein the Group VIII metal is ruthenium, rhodium or palladium.

3. A catalyst composition as claimed in claim 2 wherein the Group VIII metal is palladium.

4. A catalyst composition as claimed in claim 1 wherein $R^1$ and $R^2$ are independently fluoride.

5. A catalyst composition as claimed in claim 1 wherein $R^1$ and $R^2$ are independently phenyl.

6. A catalyst composition as claimed in claim 1 wherein $R^3$ is phenyl.

7. A catalyst composition as claimed in claim 1 wherein said metal complex is: $[F_2B(OPPh_2)_2PdCl]_2$.

8. A catalyst composition as claimed in claim 1 wherein said metal complex is: $[F_2B(OPPh_2)_2Pd(NCPh)_2]^+[BF_4]^-$.

* * * * *